(12) United States Patent
Khalapyan (10) Patent No.: US 8,956,377 B2
(45) Date of Patent: Feb. 17, 2015

(54) PUNCH TOOL

(75) Inventor: Tigran Khalapyan, Hershey, PA (US)

(73) Assignee: Empire Technology Development LLC, Wilmington, DE (US)

( * ) Notice: Subject to any disclaimer, the term of this patent is extended or adjusted under 35 U.S.C. 154(b) by 242 days.

(21) Appl. No.: 13/514,521

(22) PCT Filed: Jun. 15, 2011

(86) PCT No.: PCT/US2011/040507
§ 371 (c)(1),
(2), (4) Date: Jun. 7, 2012

(87) PCT Pub. No.: WO2012/173616
PCT Pub. Date: Dec. 20, 2012

(65) Prior Publication Data
US 2013/0012977 A1  Jan. 10, 2013

(51) Int. Cl.
*A61B 17/14* (2006.01)
*A61B 17/3205* (2006.01)
*A61B 10/02* (2006.01)

(52) U.S. Cl.
CPC ....... *A61B 17/32053* (2013.01); *A61B 10/0233* (2013.01)
USPC ...................................................... 606/184

(58) Field of Classification Search
USPC ......... 606/130, 139, 142, 143, 153, 154, 155, 606/156, 167, 184, 185
See application file for complete search history.

(56) References Cited

U.S. PATENT DOCUMENTS

| | | | | |
|---|---|---|---|---|
| 4,018,228 A | * | 4/1977 | Goosen | 606/184 |
| 5,192,294 A | * | 3/1993 | Blake, III | 606/184 |
| 5,423,848 A | * | 6/1995 | Washizuka et al. | 606/185 |
| 5,601,588 A | * | 2/1997 | Tonomura et al. | 606/185 |
| 5,676,670 A | * | 10/1997 | Kim | 606/108 |
| 5,827,316 A | | 10/1998 | Young et al. | |
| 5,893,369 A | * | 4/1999 | LeMole | 606/184 |
| 5,910,153 A | * | 6/1999 | Mayenberger | 606/184 |
| 6,022,367 A | * | 2/2000 | Sherts | 606/184 |
| 6,036,710 A | * | 3/2000 | McGarry et al. | 606/184 |

(Continued)

OTHER PUBLICATIONS

O. Chavanon et al., Increased incidence of acute ascending aortic dissection with off—pump aortocoronary bypass surgery?, The Annals of Thoracic Surgery, Jan. 2001, pp. 117-121, vol. 71, Issue 1.

(Continued)

*Primary Examiner* — Jonathan W Miles
(74) *Attorney, Agent, or Firm* — Moritt Hock & Hamroff LLP; Steven S. Rubin, Esq.

(57) ABSTRACT

Technologies are generally described for a punch tool and method of use. In an example, the punch tool may include a malleable shaft and a finger grip body configured to encompass at least part of a shaft of a finger button. The finger grip body may be connected to a first end of the malleable shaft. The malleable shaft may be adjustable to a particular conformation and to maintain the particular conformation during use of the punch tool. A second end of the malleable shaft may be connected to an anvil. The shaft of the finger button may be connected to a first end of a flexible body member. The flexible body member may be adapted to move over the malleable shaft, the movement conforming to the particular conformation of the malleable shaft. A cutter may be operatively connected to a second end of the flexible body member.

20 Claims, 4 Drawing Sheets

(56) References Cited

U.S. PATENT DOCUMENTS

| | | | | |
|---|---|---|---|---|
| 6,080,173 | A | * | 6/2000 | Williamson et al. .......... 606/184 |
| 6,176,867 | B1 | * | 1/2001 | Wright ........................ 606/184 |
| 6,290,709 | B1 | * | 9/2001 | Ellis et al. .................... 606/167 |
| 6,569,105 | B1 | * | 5/2003 | Kortenbach et al. .......... 600/562 |
| 6,652,551 | B1 | * | 11/2003 | Heiss .......................... 606/170 |
| 6,746,451 | B2 | | 6/2004 | Middleton et al. |
| 6,770,081 | B1 | | 8/2004 | Cooper et al. |
| 6,790,210 | B1 | | 9/2004 | Cragg et al. |
| 8,491,619 | B2 | * | 7/2013 | Breznock ..................... 606/184 |
| 2003/0069595 | A1 | * | 4/2003 | Phung et al. ................. 606/184 |
| 2003/0093104 | A1 | * | 5/2003 | Bonner et al. ................ 606/185 |
| 2004/0082963 | A1 | * | 4/2004 | Gannoe et al. ............... 606/153 |
| 2004/0092974 | A1 | * | 5/2004 | Gannoe et al. ............... 606/153 |
| 2009/0198153 | A1 | * | 8/2009 | Shriver ........................ 600/585 |
| 2010/0198247 | A1 | * | 8/2010 | Chang et al. ................. 606/185 |
| 2010/0228276 | A1 | * | 9/2010 | Breznock ..................... 606/185 |
| 2011/0054487 | A1 | * | 3/2011 | Farnan ......................... 606/108 |

OTHER PUBLICATIONS

Zinkernagel, M et al., Aortic dissection with potential origin from a mechanical bypass anastomosis, Ann Thorac Surg. Jul. 2005, 316-8, 80(1).

If Tabry & Em Costantini, Acute Aortic Dissection Early after Off—Pump Coronary Surgery True Frequency Underestimated?. Tex Heart Inst J. 2009, 462-467, 36(5).

Archer, G. A. et al., Aortic Dissection Following Coronary Artery Bypass Surgery: Diagnosis by CT. CardioVascular and Interventional Radiology, May, 1986, vol. 9, No. 3.

Wilson, M. J. et al., Ascending aortic atheroma assessed intraoperatively by epiaortic and transesophageal echocardiography, Ann Thorac Surg. Jul. 2000, 25-30, 70(1).

Shimokawa, T, et al., Assessment of Ascending Aorta Using Epiaortic Ultrasonography During Off—Pump Coronary Artery Bypass Grafting. Ann Thorac Surg, Dec. 2002, 2097-100, 74(6).

Lahtinen, J. et al., Fatal complications after use of the Symmetry Aortic Connector in coronary artery bypass surgery. Ann Thorac Surg. May 2004, 1817-9, 77(5).

Eckstein, FS. et al., Minimizing Aortic Manipulation During OPCAB Using the Symmetry Aortic Connector System for Proximal Vein Graft Anastomoses, Ann Thorac Surg., Sep. 2001, S995-8, 72(3).

Van Der Linden, J. et al., The Topography of Aortic Atherosclerosis Enhances Its Precision as a Predictor of Stroke. Ann Thorac Surg. Jun. 2007, 2087-92, 83(6).

Filsoufi, F. et al., Minimally invasive Cabg, Current Opinion in Cardiology 2001, 306-309, 16.

International Search Report and Written Opinion for application with application No. PCT/US2011/040507, dated Nov. 21, 2011, 14 pages.

* cited by examiner

PUNCH TOOL

CROSS REFERENCE TO RELATED APPLICATIONS

This application is a 371 of International Application No. PCT/US2011/040507 filed Jun. 15, 2011, the entirety of which is hereby incorporated by reference.

BACKGROUND

Unless otherwise expressly indicated herein, none of the material presented in this section is prior art to the claims of this application and is not admitted to be prior art by having been included herein.

A medical punch tool may be used to cut material, such as tissue. To effect a cut of material using a medical punch tool, surgical scalpels may be used to form an incision in the material. An anvil, or other support, may be inserted into the incision. Thereafter, a cutting edge of the tool may slide around the anvil and cut the material. The anvil and cutting edge of the medical punch tool may then be withdrawn from the incision.

SUMMARY

In one example, a punch tool is generally described. The punch tool may include a shaft and a finger grip body configured to encompass at least part of a shaft of a finger button, the finger grip body connected to a first end of a malleable shaft. The malleable shaft may be configured to be adjustable to a particular conformation and to maintain the particular conformation during use of the punch tool. A second end of the malleable shaft may be connected to an anvil. The shaft of the finger button may be connected to a first end of a flexible body member. The flexible body member may be adapted to move over the shaft, the movement conforming to the particular conformation of the malleable shaft. A cutter may be operatively connected to a second end of the flexible body member.

In another example, a method of using a punch tool is generally described. The method may include bending a malleable shaft to a particular conformation. The method may include inserting the punch tool into an incision at a location so that an anvil at an end of the malleable shaft defines a cutting plane. The method may include pushing a finger button along an axis oblique to the cutting plane, so that the finger button causes a flexible section to move over the malleable shaft, and causes the cutter to move with respect to the anvil.

In another example, a punch tool is generally described. The punch tool may include a finger grip body. The finger grip body may include at least one finger seat, the finger seat sized and shaped so as to be effective to receive a finger. The punch tool may include a finger button. The finger button may include a seat sized and shaped so as to be effective to receive a thumb. At least part of the finger button may be disposed internal to the finger grip body. The finger button may include a first end and a second end. The first end may be sized and shaped so as to be effective to be pushed by a finger along an axis. The finger button may include at least one wall defining a hollow cylinder. The punch tool may include a flexible body member. The flexible body member may include a first end, a second end, a flexible section, a malleable shaft, and a cutter. The first end of the flexible body member may be connected to the wall of the finger button. The flexible section may be moveable over the malleable shaft and include a wire wound in a coil. The malleable shaft may include a material such that the malleable shaft is adjustable to a particular conformation and such that the malleable shaft is effective to maintain the particular conformation during use of the punch tool. The malleable shaft may be connected to the finger grip body. The cutter may be connected to the second end of the flexible body member. The cutter may include a sleeve and an edge. The sleeve may be connected to the flexible section. The punch tool may include an anvil connected to the malleable shaft. The anvil may include a cylinder guide section, a connection section connected to the cylinder guide section, and an edge connected to the connection section.

BRIEF DESCRIPTION OF THE FIGURES

The foregoing and other features of this disclosure will become more fully apparent from the following description and appended claims taken in conjunction with the accompanying drawings. Understanding that these drawings depict only some embodiments in accordance with the disclosure and are therefore not to be considered limiting of its scope, the disclosure will be described with additional specificity and detail by reference to the accompanying drawings in which:

all arranged according to at least some embodiments described herein.

DETAILED DESCRIPTION

In the following detailed description, reference is made to the accompanying drawings which form a part thereof. In the drawings, similar symbols typically identify similar components unless context indicates otherwise. The illustrative embodiments described in the detailed description, drawings and claims are not meant to be limiting. Other embodiments may be utilized and other changes may be made without departing from the spirit or scope of the subject matter presented herein. It will be readily understood that the aspects of the present disclosure as generally described herein and as illustrated in the accompanying figures can be arranged, substituted, combined, separated and/or designed in a wide variety of different configurations all of which are explicitly contemplated herein.

This disclosure is generally drawn, inter alia, to apparatuses, systems, devices and methods relating to a punch tool.

Briefly stated, technologies are generally described for a punch tool and method of use. In an example, the punch tool may include a malleable shaft and a finger grip body configured to encompass at least part of a shaft of a finger button. The finger grip body may be connected to a first end of the malleable shaft. The malleable shaft may be adjustable to a particular conformation and to maintain the particular conformation during use of the punch tool. A second end of the malleable shaft may be connected to an anvil. The shaft of the finger button may be connected to a first end of a flexible body member. The flexible body member may be adapted to move over the malleable shaft, the movement conforming to the particular conformation of the malleable shaft. A cutter may be operatively connected to a second end of the flexible body member.

Figure 1:
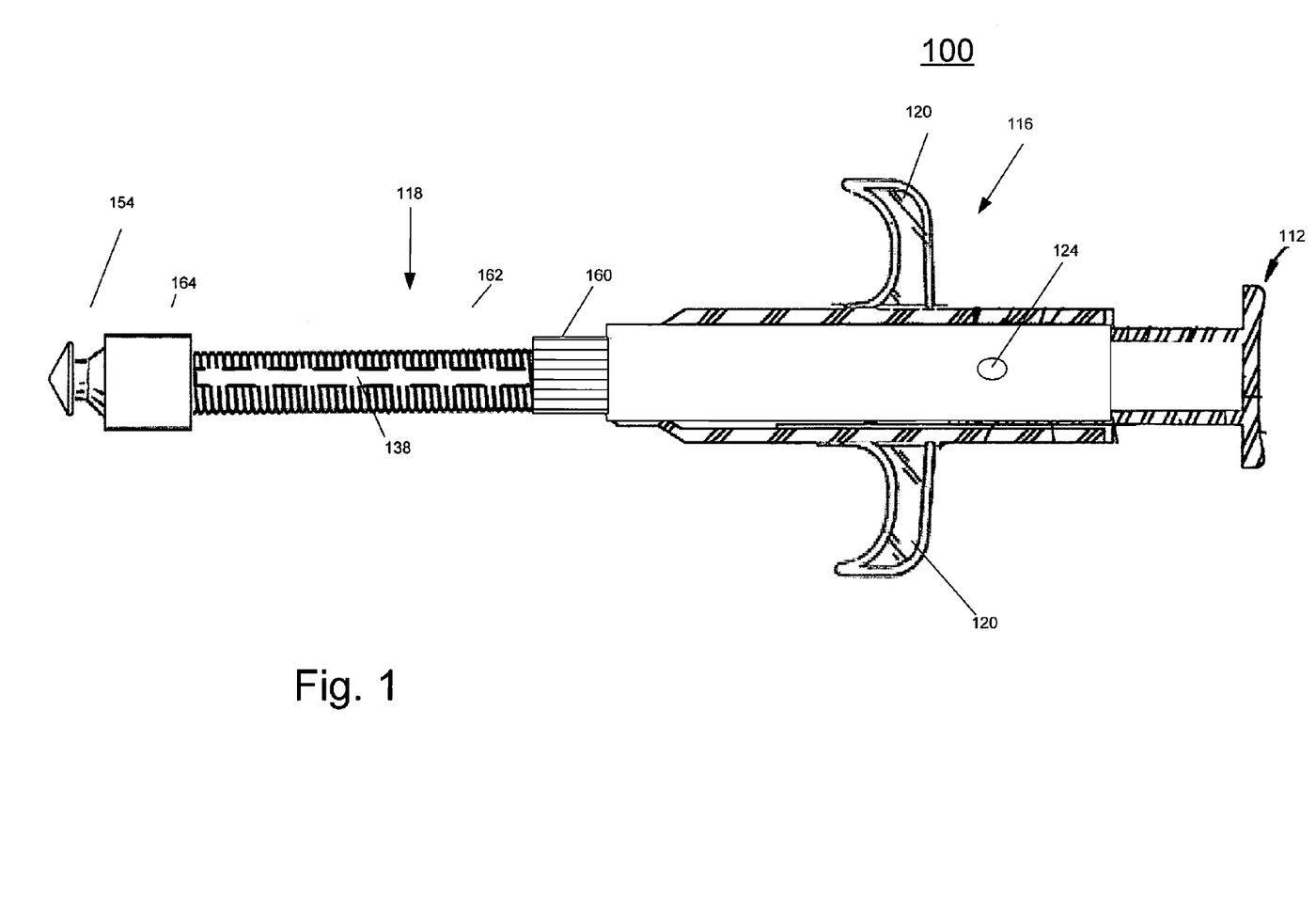
FIG. 1 is a side view of an illustrative embodiment of a punch tool.

FIG. 1 is a side view of an illustrative embodiment of a punch tool according to at least some embodiments described herein. A punch tool 100 may be shaped and designed to be utilized by a user such as a surgeon, nurse, nurse practitioner, physician's assistant, etc. using one of his or her hands. In an example, punch tool 100 may include a thumb button 112 at a first end, a finger grip body 116, a body member 118, which may be hollow, and/or an anvil 154 at a second end. Finger grip body 116 may include a pin 124 and at least one finger seat 120. Body member 118 may include a rigid section 160, a flexible section 162, a malleable shaft 138 and/or a cutter 164.

As discussed in detail below, punch tool 100 may be used to cut a hole in a tissue such as but not limited to the aorta. Body member 118 may include a malleable shaft 138 that may be bent or adjusted by a user as desired to a particular conformation. For example, malleable shaft 138 may be bent so as to position anvil 154 and cutter 164 at a desired location such as where an angle between an axis of finger grip body 116 and a plane defined by cutter 164 may be oblique such as at about 90 degrees. In examples where a user presses thumb button 112 into finger grip body 116, thumb button 112 may cause cutter 164 to move and/or slide with respect to anvil 154 and cut tissue proximate to anvil 154. In an example, malleable shaft 138 may have a diameter of about 0.06 inches to about 0.12 inches and rigid shaft 161 may have a diameter of about 0.2 inches to about 0.25 inches.

Figure 2:
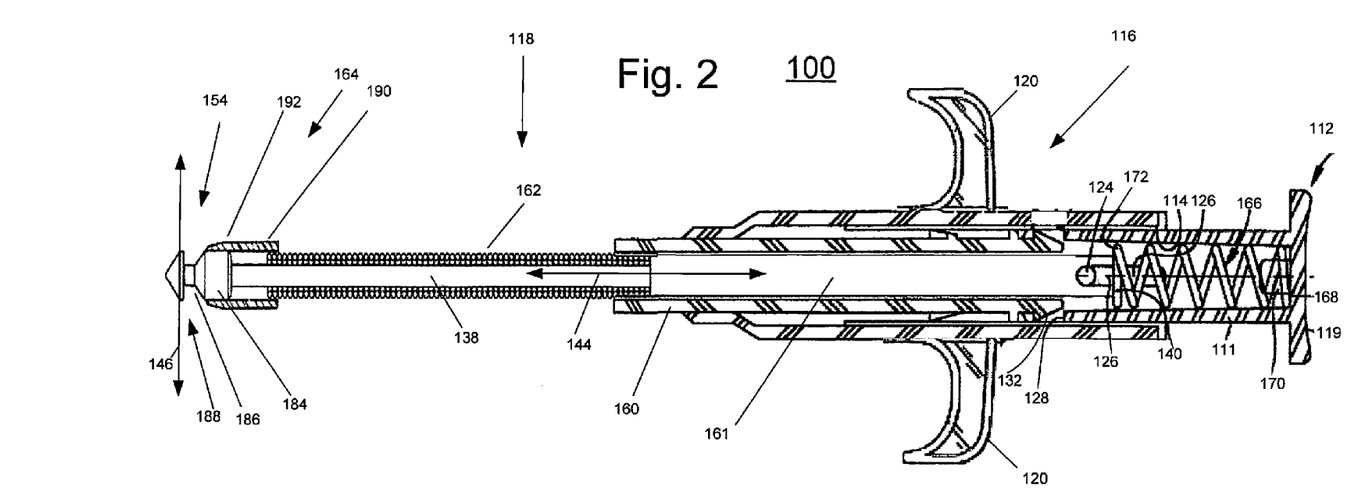
FIG. 2 is a side partially cut-away view of an illustrative embodiment of a punch tool.

FIG. 2 is a side partially cut-away view of an illustrative embodiment of a punch tool according to at least some embodiments described herein. FIGS. 3A, 3B, 3C and 3D are partially cut-away views of an illustrative embodiment of a punch tool at three distinct times according to at least some embodiments described herein. The punch tools of FIGS. 2, 3A, 3B, 3C and 3D are substantially similar to the punch tool of FIG. 1, with additional details. Those components in FIGS. 2, 3A, 3B, 3C and 3D that are labeled identically to components of FIG. 1 will not be described again for the purposes of clarity.

In an example, finger grip body 116 may be configured to encompass at least part of a shaft of thumb button 112 though any manner of providing gripping and/or moving of body member 118 may be used. Thumb button 112 may be movable into a central opening 114 of finger grip body 116. In an example, central opening 114 may be about 0.2 inches to about 0.5 inches in diameter. Thumb button 112 may include a thumb seat 119. Thumb seat 119 may be sized and shaped so as to be engaged by the thumb of the user. Thumb button 112 may include a hollow cylindrical portion 111 which extends into central opening 114 of finger grip body 116. Cylindrical portion 111 may include walls defining slots 126 and may, in an example, be about 0.1 inches to about 0.4 inches in diameter. Pin 124 may be received in slots 126. Pin 124 may be effective to slide in slots 126 when thumb button 112 is pushed into opening 114 of finger grip body 116. As thumb button 112 is pushed into central opening 114 in finger grip body 116, engagement of pin 124 with walls defining slots 126 may restrict the extent to which thumb button 112 can be pushed into central opening 114. Finger grip body 116 may include at least one finger seat 120 and may be made of plastic. Finger seat 120 may be sized and shaped so as to be effective to receive one or more fingers of a user.

Thumb button 112 may include walls terminating in a bottom portion 128 and may be made of plastic. Bottom portion 128 may be connected to a top portion 132 of rigid section 160 of body member 118. Rigid section 160 may be made of plastic. This connection may provide that flexible section 162 of body member 118 may move when thumb button 112 is moved in central opening 114 of finger grip body 116.

Malleable shaft 138 may be connected to anvil 154 and extend through body member 118 and finger grip body 116. Pin 124 may extend through, and secure, a top portion 140 of a rigid shaft 161 connected to malleable shaft 138. Rigid shaft 161 may be made of plastic. Rigid shaft 161 and malleable shaft 138 may form a combined shaft for punch tool 100. Malleable shaft 138 and rigid shaft 161 may be adapted to remain stationary with respect to the finger grip body 116 when thumb button 112 is pushed into central opening 114 of finger grip body 116.

Inside walls of thumb button 112 may sit a compression spring 166. A top 168 of compression spring 166 may be connected to a flange 170 disposed within hollow cylindrical portion 111 of thumb button 112. A bottom 172 of compression spring 166 may be connected to top portion 140 of rigid shaft 161. Compression spring 166 may be effective to apply a force to thumb button 112 to push thumb button 112 outward from central opening 114 of finger grip body 116.

At a second end of body member 118 may be cutter 164 and anvil 154. Anvil 154 may include a cylindrically shaped guide section 184, a connection part 186, and/or a cutting part 188. In an example, diameters of guide section 184 and cutting part 188 may be substantially equal and may be between about 2.0 mm and about 6.5 mm. A diameter of connection part 186 may be about 0.05 inches to about 0.1 inches. In an example, cutter 164 may be about 0.6 inches long and have an outer diameter of about 0.3 inches.

Malleable shaft 138 may be connected to guide section 184 of anvil 154. Cutter 164 may include a sleeve 190 and a cutting edge 192 though any structure may be used to perform a cut. Cutting edge 192, in combination with cutting part 188, may form a cutting tool. Cutting part 188 may define a cutting plane 146 for punch tool 100. An external diameter of guide section 184 may substantially correspond to an inner diameter of sleeve 190 and to an outer diameter of cutting part 188. An end of flexible section 162 may be securely connected to a first end of sleeve 190. As explained below, flexible section 162 may be adapted to move and/or slide over malleable shaft 138. Sleeve 190 may be moveable over guide section 184. In an example, cutter 164 and anvil 154 may be made of stainless steel.

Malleable shaft 138 may be configured so as to be adjustable to a particular conformation and to maintain that particular conformation during use of the punch tool. For example, the particular conformation may define an oblique angle between an axis of finger grip body 116 and a plane defined by cutter 164. For example at least a part of malleable shaft 138 may be made of a malleable material so that malleable shaft 138 may be bent and adjusted to a desired conformation by a user and malleable shaft 138 may maintain that conformation during use of punch tool 100. Malleable shaft 138 may be made of a material of sufficient strength so as to retain a bend or conformation defined by the user. In an example, malleable shaft 138 may be made of a type 302 or 303 annealed stainless steel wire. In this example, malleable shaft 138 may include about 0% to about 0.15% carbon, about 0% to about 2% manganese, about 0% to about 0.2% phosphorous, about 0% to about 0.15% sulphur, from about 0% to about 1% silicon, from about 17% to about 19% chromium, from about 8% to about 10% nickel, and/or from about 0% to about 0.6% molybdenum. In an example, malleable shaft 138 may be made of an anodized aluminium alloy. In an example, malleable shaft 138 may be made of a memory type metal such as a nickel-titanium alloy sometimes known as NITINOL. In some examples, such memory metals may be effective to be bent by a user and then restored to their original configuration during a heating or sterilization process.

In an example, flexible section 162 may be made of a flexible spring-type wire wound in a coil. Such a configuration may provide flexibility and strength sufficient to transmit axial forces along axis 144 from rigid section 160 of body member 118 to cutter 164. In an example, flexible section 162 may be made of steel or stainless steel wires wound in a coil or helix, or a material such as an ELGILOY cobalt alloy wire. As mentioned above, flexible section 162 may be moveable over malleable shaft 138. Flexible section 162 may conform to a particular conformation of malleable shaft 138 and may move over malleable shaft 138 even when malleable shaft 138 is bent. An inside diameter of flexible section 162 may be larger than an outside diameter of malleable shaft 138 to facilitate movement of flexible section 162 with respect to malleable shaft 138. In an example, an outer diameter of flexible section 162 may be about 0.15 inches to about 0.3 inches, an inner diameter may be about 0.1 inches to about 0.2 inches, and a diameter of coiled wire forming flexible section 162 may be about 0.01 inches to about 0.1 inches.

Figures 3A, 3B:
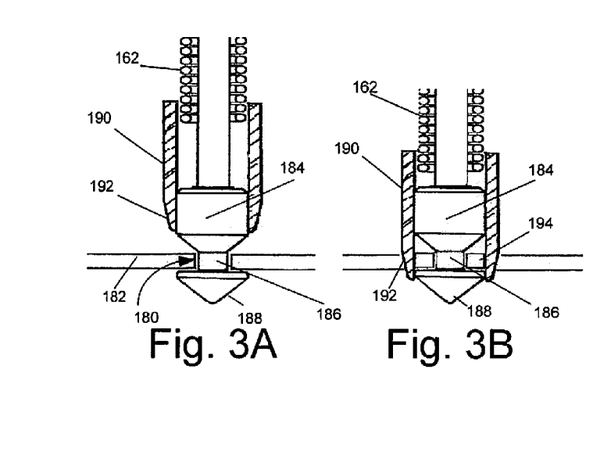
FIGS. 3A, 3B, 3C and 3D are side partially cut-away views of an illustrative embodiment of a punch tool at three distinct times.
Figure 3C:
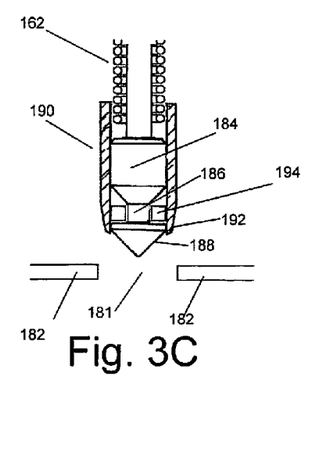
Figure 3D:
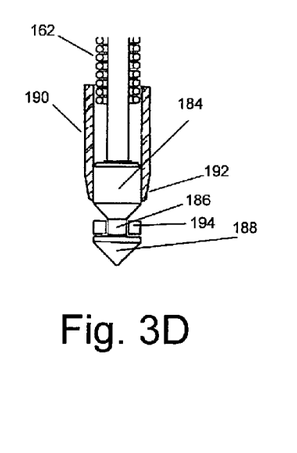

Focusing on FIG. 3A, in use, an incision 180 may be made in a tissue 182. Cutting part 188 may be inserted into incision 180. Thumb button 112 may be pushed into finger grip body 116 along axis 144, thereby moving rigid section 160 and flexible section 162 over malleable shaft 138. Movement of flexible section 162 may impart movement of sleeve 190 and cutting edge 192. Cutting edge 192 of cutter 164 may move over cutting part 188 of anvil 154 thereby creating a cut 194 of tissue 182 and a hole 181 as shown at FIGS. 3B and 3C. A size of cut 194 may correspond to a diameter of cutting part 188 and may have a disc-shaped cross-section. When a user releases thumb button 112, spring 116 may be effective to push thumb button 112 out of finger grip body 116. Movement of thumb button 112 out of finger grip body 116 may cause sleeve 190 and cutting edge 192 to move away from anvil 154 and toward a resting position as shown at FIG. 3D.

Figure 4:
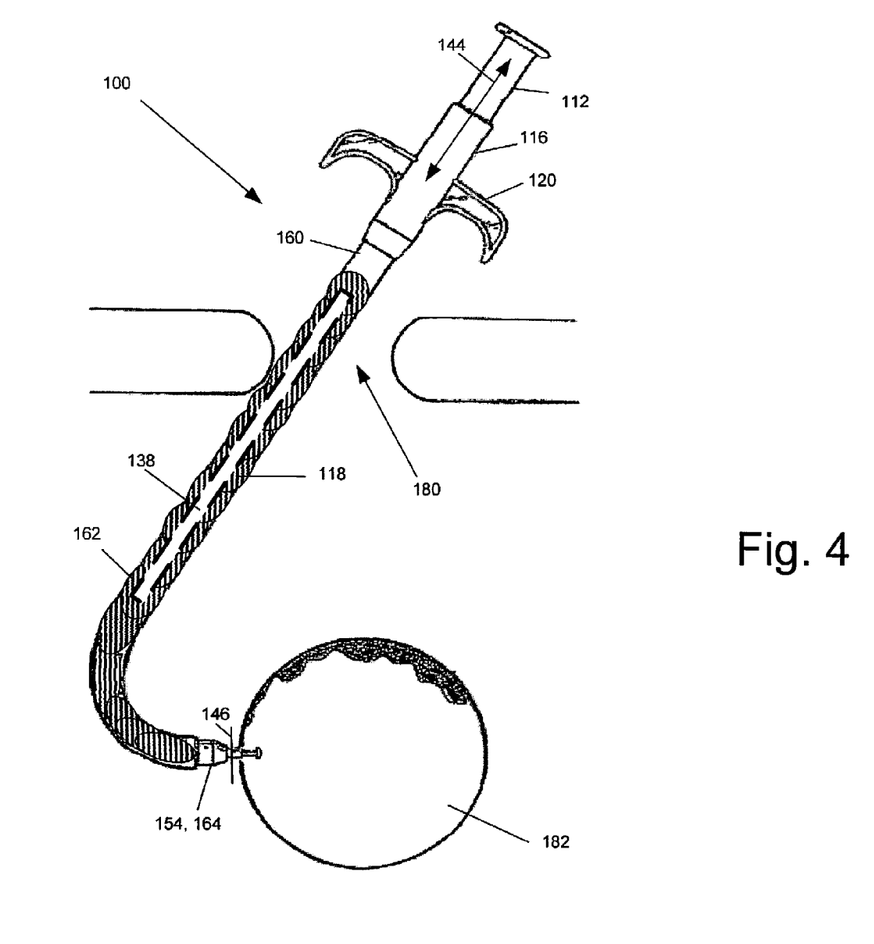
FIG. 4 is a side view of an illustrative embodiment of a punch tool.

FIG. 4 is a side view of an illustrative embodiment of a punch tool according to at least some embodiments described herein. The punch tool of FIG. 4 is substantially similar to the punch tool of FIGS. 1, 2 and 3 with additional details. Those components in FIG. 4 that are labelled identically to components of FIGS. 1, 2 and 3 will not be described again for the purposes of clarity.

A shape of a punch tool in accordance with the disclosure may be changed before a user inserts the punch tool. Body member 118 may be bent to a particular conformation so that anvil 154 defines a cutting plane 146 that is oblique to axis 144. Cutter 164 may be oriented to a position that is substantially perpendicular to a plane of tissue 182. As shown in FIG. 4, a user may insert punch tool 100 in an incision 180 after flexible section 162 is bent or curved. As malleable shaft 138 may be malleable, punch tool 100 may be used even in difficult to access target areas. As body member 118 may be flexible, cutter 164 may be used even when malleable shaft 138 is bent or curved.

Among other possible benefits, a shape of a punch tool in accordance with the disclosure may be changed before a user inserts the punch. In some embodiments, the shape of the punch tool may be modified after the tool has been inserted. This may be facilitated, for example, by grasping the internal end using another appropriate surgical device, or through manipulation from an external location. The punch tool may be inserted through relatively small incision areas as may be used in minimally invasive surgery. A punch tool may be used in areas which may be otherwise difficult to access such as where a punch tool is desired as a location with a plane that is not 90 degrees from a surgical incision. A user may be able to use a punch tool and may be able to avoid manipulating organs or tissue to reach a desired organ.

Figure 5:
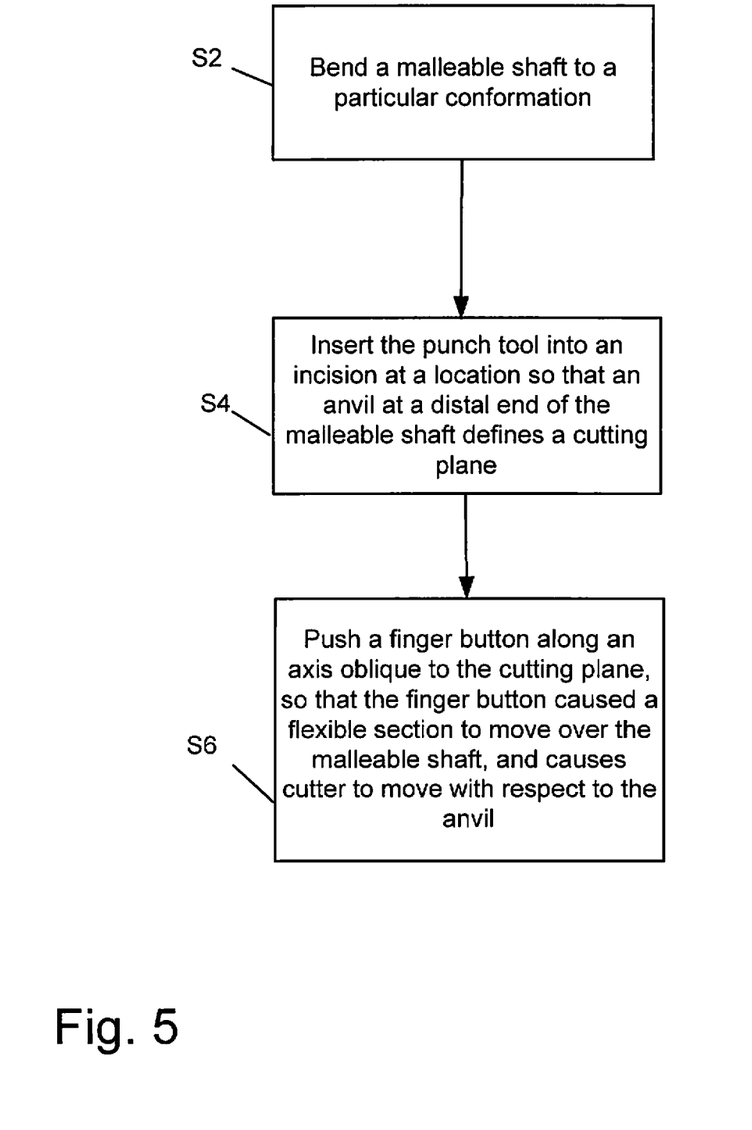
FIG. 5 depicts a flow diagram for example processes for using a punch tool.

FIG. 5 depicts a flow diagram for example processes for using a punch tool in accordance to at least some embodiments described herein. An example process may include one or more operations, actions, or functions as illustrated by one or more of blocks S2, S4 and/or S6. Although illustrated as discrete blocks, various blocks may be divided into additional blocks, combined into fewer blocks, implemented in alternate orders, repeated, or eliminated, depending on the desired implementation.

At block S2, a user may bend a malleable shaft to a particular conformation.

At block S4, a user may insert the punch tool into an incision at a location so that an anvil at a second end of the malleable shaft defines a cutting plane.

At block S6, a user may push a finger button along an axis oblique to the cutting plane, so that the finger button causes a flexible section to move over the malleable shaft, and causes the cutter to move with respect to the anvil.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A punch tool comprising:
    a finger grip body configured to encompass at least part of a shaft of a finger button, the finger grip body connected to a first end of a malleable shaft;
    an anvil connected to a second end of the malleable shaft, wherein the malleable shaft is configured to be adjustable to a particular conformation such that an oblique angle is formed between an axis of the finger grip body and a cutting plane defined by the anvil and the malleable shaft is further configured to maintain the particular conformation before insertion and during use of the punch tool;
    wherein the shaft of the finger button is connected to a first end of a flexible body member, the flexible body member adapted to move over the malleable shaft, the movement in conformance with the particular conformation of the malleable shaft, and
    wherein a cutter is operatively connected to a second end of the flexible body member so that movement of the flexible body member over the malleable shaft is effective to impart movement of the cutter with respect to the malleable shaft.

2. The punch tool as recited in claim 1, wherein the finger grip body further includes at least one finger seat, the finger seat sized and shaped so as to be effective to receive a finger.

3. The punch tool as recited in claim 1, wherein the finger button includes a seat sized and shaped so as to be effective to receive a thumb.

4. The punch tool as recited in claim 1, further comprising a rigid section disposed between the finger grip body and the flexible body member, wherein the rigid section includes a first end and a second end, the first end of the rigid section being connected to the finger button, the second end of the rigid section being connected to the flexible section of the flexible body member.

5. The punch tool as recited in claim 1, wherein the finger button includes at least one wall defining a hollow cylinder, and wherein the wall of the finger button is connected to the flexible section of the flexible body member.

6. The punch tool as recited in claim 1, wherein the anvil comprises:
    a cylinder guide section;
    a connection section connected to the cylinder guide section; and
    an edge connected to the connection section.

7. The punch tool as recited in claim 6, wherein the cutter includes a sleeve and an edge, wherein the sleeve is connected to the flexible section, and wherein a diameter of the cylinder guide section is substantially equally to an inner diameter of the sleeve.

8. The punch tool as recited in claim 1, wherein the cutter comprises a sleeve and an edge, wherein the sleeve is connected to the flexible section.

9. The punch tool as recited in claim 1, wherein the malleable shaft comprises type 302 or 303 annealed stainless steel wire.

10. The punch tool as recited in claim 1, wherein the malleable shaft includes about 0% to about 0.15% carbon, about 0% to about 2% manganese, about 0% to about 0.2% phosphorous, about 0% to about 0.15% sulfur, about 0% to about 1% silicon, about 17% to about 19% chromium, about 8% to about 10% nickel, and about 0% to about 0.6% molybdenum.

11. The punch tool as recited in claim 1, wherein the malleable shaft includes a memory metal.

12. The punch tool as recited in claim 1, wherein the malleable shaft includes a nickel-titanium alloy.

13. The punch tool as recited in claim 1, wherein the flexible section includes a wire wound in a coil.

14. The punch tool as recited in claim 13, wherein the flexible section includes steel, stainless steel or a cobalt alloy wire.

15. The punch tool as recited in claim 1, wherein the finger button is effective to be pushed along an axis, and wherein the anvil is effective to define a cutting plane oblique to the axis.

16. A method of using a punch tool, the method comprising:
   bending a malleable shaft to a particular conformation before insertion;
   inserting the punch tool into an incision at a location so that an anvil at an end of the malleable shaft defines a cutting plane;
   pushing a finger button along an axis oblique to the cutting plane, so that the finger button causes a flexible section to move over the malleable shaft conforming to the particular conformation, and the movement of the flexible section causes the cutter to move with respect to the anvil.

17. The method as recited in claim 16, wherein the malleable shaft is configured to be adjustable to the particular conformation and to maintain the particular conformation during use of the punch tool.

18. The method as recited in claim 17, wherein the malleable shaft comprises type 302 or 303 annealed stainless steel wire including about 0% to about 0.15% carbon, about 0% to about 2% manganese, about 0% to about 0.2% phosphorous, about 0% to about 0.15% sulfur, about 0% to about 1% silicon, about 17% to about 19% chromium, about 8% to about 10% nickel, and about 0% to about 0.6% molybdenum; and
   the flexible section includes a wire wound in a coil.

19. A punch tool comprising:
   a finger grip body, wherein the finger grip body includes at least one finger seat, the finger seat sized and shaped so as to be effective to receive a finger;
   a finger button, wherein the finger button includes a seat sized and shaped so as to be effective to receive a thumb, wherein at least part of the finger button is disposed internal to the finger grip body, the finger button includes a first end and a second end, the first end sized and shaped so as to be effective to be pushed by a finger along an axis, the finger button includes at least one wall defining a hollow cylinder,
   a flexible body member, wherein the flexible body member includes a first end, a second end, a flexible section, a malleable shaft, and a cutter, wherein
      the first end of the flexible body member is connected to the wall of the finger button;
      the malleable shaft includes a material such that the malleable shaft is adjustable to a particular conformation and such that the malleable shaft is effective to maintain the particular conformation before insertion and during use of the punch tool,
      the flexible section is moveable over the malleable shaft in conformance with the particular conformation, the flexible section includes a wire wound in a coil;
      the malleable shaft is connected to the finger grip body;
      the cutter is connected to the second end of the flexible body member so that movement of the flexible body member over the malleable shaft is effective to impart movement of the cutter with respect to the malleable shaft, the cutter includes a sleeve and an edge, wherein the sleeve is connected to the flexible section; and
   an anvil connected to the malleable shaft, wherein the anvil includes
      a cylinder guide section,
      a connection section connected to the cylinder guide section, and
      an edge connected to the connection section.

20. The punch tool as recited in claim 19, wherein the malleable shaft comprises a nickel-titanium alloy or a type 302 or type 303 annealed stainless steel wire, wherein the type 302 or type 303 annealed stainless steel wire includes about 0% to about 0.15% carbon, about 0% to about 2% manganese, about 0% to about 0.2% phosphorous, about 0% to about 0.15% sulfur, about 0% to about 1% silicon, about 17% to about 19% chromium, about 8% to about 10% nickel, and about 0% to about 0.6% molybdenum.

* * * * *

UNITED STATES PATENT AND TRADEMARK OFFICE
CERTIFICATE OF CORRECTION

PATENT NO.         : 8,956,377 B2                                         Page 1 of 1
APPLICATION NO.    : 13/514521
DATED              : February 17, 2015
INVENTOR(S)        : Khalapyan It is certified that error appears in the above-identified patent and that said Letters Patent is hereby corrected as shown below:

In the Specification

In Column 1, Line 6, delete "is a 371 of" and insert -- is a U.S. national stage filing under 35 U.S.C. § 371 of --, therefor.

In Column 5, Line 36, delete "spring 116" and insert -- spring 166 --, therefor.

Signed and Sealed this
Eighth Day of September, 2015

Michelle K. Lee
*Director of the United States Patent and Trademark Office*